United States Patent [19]

Ballies

[11] Patent Number: 4,643,198
[45] Date of Patent: Feb. 17, 1987

[54] CAP FOR A TUBE FOR EXTRACTING BLOOD

[76] Inventor: Uwe Ballies, Jagersberg 7-9, D-2300 Kiel, Fed. Rep. of Germany

[21] Appl. No.: 578,701

[22] Filed: Feb. 9, 1984

[30] Foreign Application Priority Data

Feb. 12, 1983 [DE] Fed. Rep. of Germany ... 8304179[U]

[51] Int. Cl.[4] .............................................. A61B 5/14
[52] U.S. Cl. .................................... 128/763; 604/221; 604/228; 604/236; 604/249
[58] Field of Search ............. 128/752, 753, 754, 758, 128/760, 763, 765, 766; 604/236, 249, 221, 228, 229, 240, 241; 222/631, 319, 322, 380, 402.23, 402.25; 251/DIG. 1, 61.3, 63.6, 61.5; 215/5, 272, DIG. 3

[56] References Cited

U.S. PATENT DOCUMENTS

| | | | |
|---|---|---|---|
| 3,064,696 | 11/1962 | Gruenewald | 222/402.25 |
| 3,223,173 | 12/1965 | Paul, Jr. | 222/402.25 |
| 3,480,009 | 11/1969 | Sinai | 604/236 |
| 3,754,644 | 8/1973 | Hampel | 604/228 |
| 4,194,653 | 3/1980 | Brown | 222/402.25 |
| 4,215,701 | 8/1980 | Raitto | 128/763 |
| 4,320,770 | 3/1982 | Etherington et al. | 128/765 |
| 4,326,541 | 4/1982 | Eckels | 128/766 |
| 4,479,592 | 10/1984 | Rusing et al. | 222/319 |

Primary Examiner—William E. Kamm
Attorney, Agent, or Firm—Cushman, Darby & Cushman

[57] ABSTRACT

A blood extraction cannula cap is provided with a skirt which can be inserted over a tube for receiving the blood, the upper portion of the skirt being closed and having a cannula bore for receiving a needle and a push button resiliently mounted on the end of the cap with the push button being connected to a closing member which closes a bore connecting the cannula to the interior of the cap.

16 Claims, 4 Drawing Figures

CAP FOR A TUBE FOR EXTRACTING BLOOD

BACKGROUND OF THE INVENTION

The invention relates to a cap for a tube for extracting blood or the like, with a base, a cannula cone placed on the base and a skirt connected to the base having a locking mechanism for fixing the cap to the cylindrical body of the tube.

It is already known to provide injection syringes with a removable cap, to make it possible to better clean a syringe, which is intended for use more than once. Moreover, a removable cap makes it possible to adapt cannulas of different diameters to the same injection syringe cylinder. The attachment and locking of the cap to the injection syringe cylinder is normally effected with a thread, where the cap skirt is provided with an internal thread and the lower end of the syringe cylinder with an external thread. However, it is also possible to use bayonet catches and spring catches as a locking element.

If such an injection syringe is used for extracting blood, the doctor or nurse sticks the cannula with the plunger or piston rod initially completely depressed in the direction of the cap into the vein of a patient and then raises the piston rod connected to the syringe piston. As a result of this raising or pulling up action, the blood is sucked into the syringe cylinder. This requires two hands, because the syringe inserted in the vein must be held with one hand, whilst the other hand is used for raising the piston.

SUMMARY OF THE INVENTION

The problem of the invention is to provide an improved cap for a blood extraction tube, which permits one-handed operation during the removal of a liquid from a vessel, particularly when removing blood from a vein.

According to the invention, this problem is solved by a cap of the aforementioned type, wherein a closing member is inserted in the cap skirt and in the inoperative position closes a cannula bore leading to the cannula cone by means of a closing surface, releasing the cannula bore by depressing an actuating element. The actuating element is preferably a pushbutton, a key, a lever or a similar element.

Thus, the piston of a tube provided with a cap according to the invention and for example a tube in accordance with DE-OS No. 2,711,366 can be raised and locked in the raised position before sticking its cannula into the blood vessel of a patient, or into any vessel, e.g., a bottle, cup, etc. containing a treatment fluid. The closing member keeps the cannula bore closed, so that a vacuum is formed in the cylindrical body of the tube and this is vented on depressing the pushbutton acting on the closing member. If at the time of depressing the closing member, the cannula mounted on the cap is immersed in blood or some other liquid, the latter is sucked into the tube by the vacuum. This suction action can be done with one hand, because one finger of the hand holding the syringe is all that is required for depressing the pushbutton.

Other advantageous developments of the invention can be gathered from the subclaims and the following specific description.

BRIEF DESCRIPTION OF THE DRAWINGS

The invention is described in greater detail hereinafter relative to non-limitative embodiments and the attached drawings, which show.

DETAILED DESCRIPTION OF THE PREFERRED EMBODIMENTS

Figure 1:
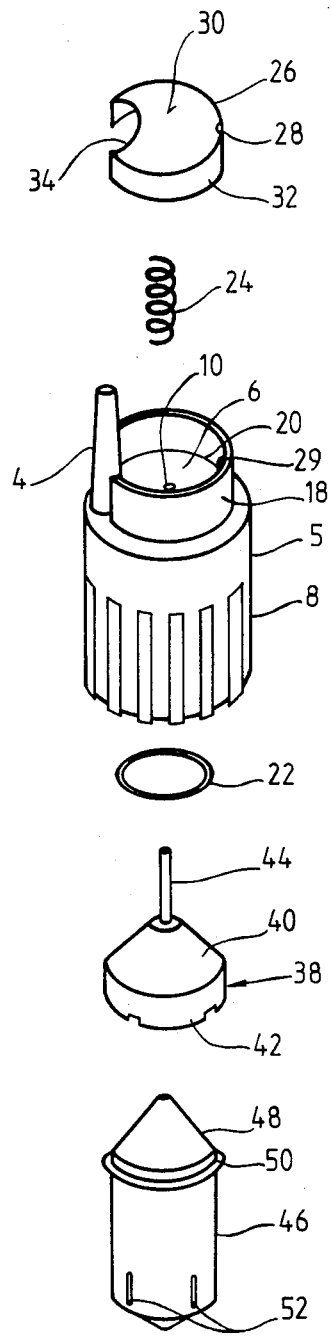
FIG. 1 an exploded view of a first embodiment.

Throughout the drawings, the same parts carry the same reference numerals. FIG. 1 is an exploded view of a cap 1, which is placed with an air tight fit on the end of a blood extraction tube or vessel 2 indicated by dot-dash lines in FIG. 2. According to FIG. 1, cap 1 has six components and specifically from top to bottom a pushbutton 26, a compression spring 24, a cap body 5, an O-ring 22, a closing member 38 and a separating member 46. With the exception of compression spring 24 and O-ring 22, all the other components can easily be produced by injection molding.

Figure 2:
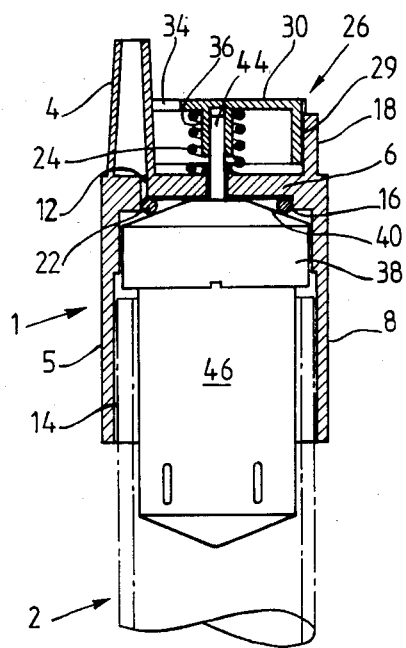
FIG. 2 a vertical section through the first embodiment.
Figure 3:
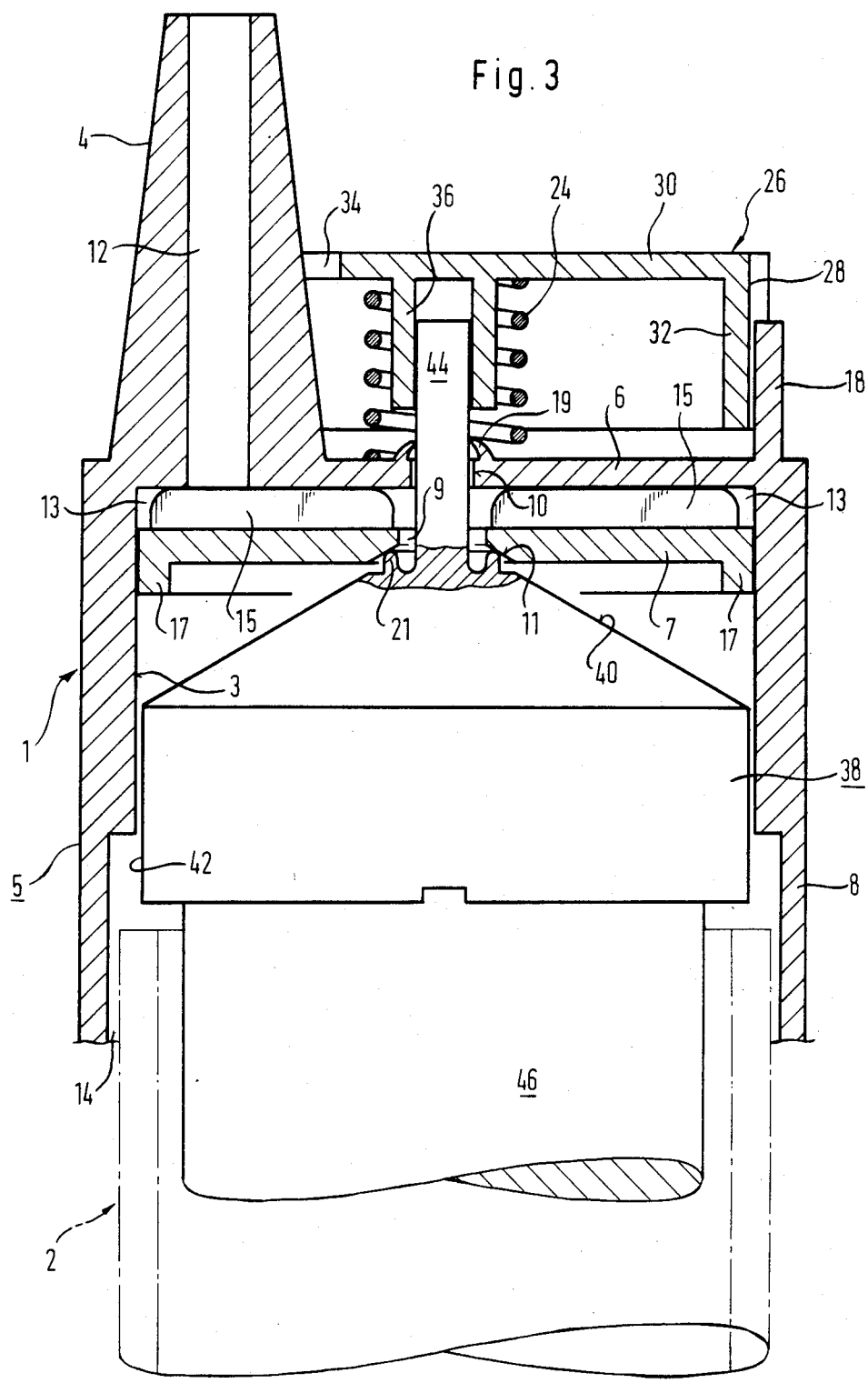
FIG. 3 a vertical section, similar to FIG. 2, but through a second embodiment.

Separating member 46 shown in FIGS. 1 to 3 is a cylindrical solid body having guidance projections 52 on its lower edge. The external diameter of separating member 46 must be chosen in such a way that it is easily movable in the interior of a blood extracting tube 2 in which it is guided by guidance projections 52. In one construction, there are four longitudinal guidance projections 52 oriented in the axial direction of the separating member 46. At its upper end opposite to the guidance projections 52, separating member 46 has an upper edge 50 for receiving the closing member 38. Above upper edge 50, separating member 46 is terminated by a conical tip 48. Separating member 46 is not absolutely necessary for the operation of the cap according to the invention. The closing member has a smaller outer diameter than the corresponding interior diameter of the cap 5.

Onto the conical cylindrical tip 48 of separating member 46 can be placed the closing member 38, which has a conical closing surface 40 and a cylindrical portion 42 connected to the base of the conical closing surface 40. The internal diameter of cylindrical portion roughly corresponds to the external diameter of the upper edge 50 extending in the form of a circumferential flange around separating member 46, so that cylindrical portion 42 snaps over the upper edge 50 for locking relative to separating member 46. The cone angle of closing surface 40 roughly corresponds to the cone angle of cylindrical tip 48, so that the closing member 38 snapped over the upper edge 50 is supported by the cylindrical conical tip 48. Onto the upper end of closing surface 40 is provided a tip 44, which is shaped like a cylindrical rod.

Cap body 5 has a base 6, which carries an eccentrically arranged cannula cone 4 and onto its side remote from cone 4 is connected a skirt 8, which is internally provided with an internal thread 14 for locking or fixing to the tube 2. Cannula cone 4 has a cannula bore 12, which extends through base 6 and consequently brings the interior of cap body 5 into flow connection with cannula cone 4. The cannula bore 12 issues into the vicinity of a shoulder 16 in base 6, in such a way that an O-ring 22 placed on the inside of base 6 and supported by shoulder 16 is able to cover bore 12.

An annular wall 18 surrounds the central bore 10 on the side of base 6 facing cannula cone 4. The diameter of central bore 10 is slightly larger than the external diameter of tip 44 of closing member 38 and the oversize can be selected without difficulty by those skilled in this art. A few tenths of a millimeter are generally sufficient to allow a free displaceability of tip 44 in central bore 10. The height of wall 18, measured in the axial extension of cap 1, is chosen in such a way that it permits the guidance of pushbutton 26.

Pushbutton 26 is a substantially cylindrical cap with a cover 30, which is closed with the exception of a cutout 34 and to which is connected a cylindrical side wall 32. Cutout 34 is provided at the location of the cannula cone 4, so that despite the eccentrically fitted cone 4, it makes it possible to depress pushbutton 26. A groove 28 (FIG. 3) running in the direction of a generatrix of side wall 32 diametrically faces cutout 34, so that groove 28 extends over the entire height of side wall 32. With pushbutton 26 fitted, an axial projection 29 provided on the inside of wall 32 engages in the groove 28 and prevents rotation of pushbutton 26, although permitting an axial displacement. A pin receiver 36 in the form of a hollow cylinder is shaped onto the bottom of cover 30 of pushbutton 26 and its height is roughly the same as that of side wall 32. The internal diameter of pin receiver 36 is such that it can be force-fitted onto the tip 44 of closing member 38 so as to be securely held thereby and movable therewith. This leads to a force-locked connection between closing member 38 and pushbutton 26.

Between cover 30 of pushbutton 26 and base 6 of cap body 5 is inserted a compression spring 24 surrounding pin receiver 36 and which normally presses the pushbutton 26 away from base 6 and consequently draws the closing member 38 against the bottom of base 6. Through an appropriate choice of the cone angle of closing surface 40, it is possible to seal O-ring 22 with closing surface 40 and press the same against base 6. Thus, O-ring 22 is forced onto the cannula bore 12, so that the interior cannula cone 4 is closed. There is also a sealing of central bore 10, because none of the air between O-ring 22 and closing surface 40 can pass into the space surrounded by skirt 8. Obviously, cannula bore 12 need not be at the support point of O-ring 22 and need merely be arranged within the radial width of the latter. By a corresponding construction of the contact surfaces for closing surface 40, it is also possible to bring about such a seal without the O-ring and as is the case with the construction according to FIGS. 3 or 4.

According to the invention, cap 1 is fitted by initially pressing closing member 38 onto separating member 46. The O-ring 22 is then placed in the depression formed by shoulder 16 in base 6. Tip 44 is then passed through the central bore 10 of base 6, so that it projects out of base 6 within wall 18. The compression spring 24 is then placed over tip 44 and then the pushbutton 26 is forced onto tip 44 until depression of pushbutton 26 is still possible when closing surface 40 rests completely on O-ring 22. A sealing collar 19 (FIG. 3) seals the tip 44 relative to the central bore 10.

The thus fitted cap 1 can now be screwed, inserted or in some other way fitted to the blood extraction tube 2. For operation purposes, a per se known, not shown piston with its piston rod is placed in the cylinder end remote from cap 1 and is secured by a further, also known cap, which appropriately has a locking mechanism for holding the raised piston in the raised position. This is achieved in per se known manner in that the piston rod has thickened portions which, in the case of a powerful pulling action, can be moved through the cap and prevents any slipping back of the piston. If the pulling up and locking of the piston takes place with pushbutton 26 unactuated, a vacuum is formed in tube 2 which makes the cannula ready to operate. For sticking into a blood vessel or the like, a needle is placed on cannula cone 4 and the thus assembled syringe can be inserted in the vessel one-handed. The pushbutton 26 is then depressed with one finger, e.g., the index finger, so that the blood or liquid in the cannula and cannula cone 4 is rapidly sucked by the cannula bore 12 into the tube 2 as a result of the vacuum in the latter.

After removing the vacuum, O-ring 22 again closes the cannula bore 12 and prevents the escape of blood therefrom. By sealing pushbutton 26 it is possible to prevent the removal of blood.

If the blood contained in the cylinder is to be centrifuged, separating member 46 can be held in locking engagement with the closing member 38 and consequently in the position according to FIG. 2 by means of its upper edge 50 and up to a predetermined g-number, whilst a preseparation of the blood constituents takes place. Only on exceeding the predetermined g-number is the separating member 46 released from the closing member 38, as is described e.g. in U.S. Pat. No. 4,154,690, the disclosure of which is incorporated herein by reference.

FIG. 3 shows the second embodiment, in which the cannula bore 12 is closed by a valve seat 11 provided in a flat partition 7, instead of by an O-ring 22. Partition 7 has formed thereon a number of ribs 15 on one side which faces the base 6 when mounted. Preferably there are six ribs which surround a middle bore 9 of the partition 7 and extend radially relative thereto. The ribs 15 are spaced advantageously with a distance between the periphery 17 of the partition 7 and the perimeter of the middle bore 9 to allow free distribution of the blood sucked into a flow channel 13 formed between the base 6 and the partition 7. The middle bore 9 has a diameter of a size so that the tip 44 of the closing member 38 can freely pass therethrough and that further there is an unobstructed blood flow path through an annular space formed between the tip 44 and the wall of the middle bore 9. Preferably the diameter of the middle bore 9 is 1.5 to two times larger than the external diameter of the tip 44. Middle bore 9 is aligned with the central bore 10 in base 6, so that the tip 44 of closing member 38 can simultaneously extend through middle bore 9 and central bore 10 without tilting or jamming. Central bore 10 has a smaller diameter than middle bore 9 but a slightly larger diameter than tip 44, so that tip 44 can actually slide within central bore 10 with slight friction. To seal the tip 44 a sealing collar 19 is provided on the outer side of base 6 which faces the pushbutton 26, which sealing collar 19 prevents blood from leaking from the space between central bore 10 and tip 44. To effect the sealing action the upper rim of the sealing collar 19 engages the circumference of tip 44 which preferably has a cylindrical cross-section for this sealing purpose.

The periphery 17 of flat partition 7 extends a little bit downwardly in the shown embodiment in the direction towards tube 2 to achieve better contacting of inner wall 3 of cap 1 and to prevent tilting and jamming of partition 7 when inserting into cap 1. Middle bore 9 is surrounded by the valve seat 11 which widens downwards and outwards and therefore faces the opposite direction of partition 7 than the ribs 15 face, so that its valve seat surface is part of a conical surface for a ring collar 21 which surrounds the base of tip 44 and thereby forms the end of closing surface 40 adjacent to tip 44. In the embodiment of FIG. 3 opening or closing of the valve is therefore effected by ring collar 21 instead of closing surface 40, which ring collar is pressed against valve seat 11 by the action of the compression spring 24 acting on the ring collar 21 through pin receiver 36 and tip 44 frictionally secured thereto by a force fit as in the embodiment of FIGS. 1 and 2. Opening of the valve is effected by simply pressing pushbutton 26 which lifts ring collar 21 from valve seat 11 and allows blood to flow from cannula bore 12 through flow channel 13 and through middle bore 9 into tube 2. When pressure on pushbutton 26 is released, spring 24 moves the pushbutton upwardly to raise surface 40 and ring collar 21.

Figure 4:
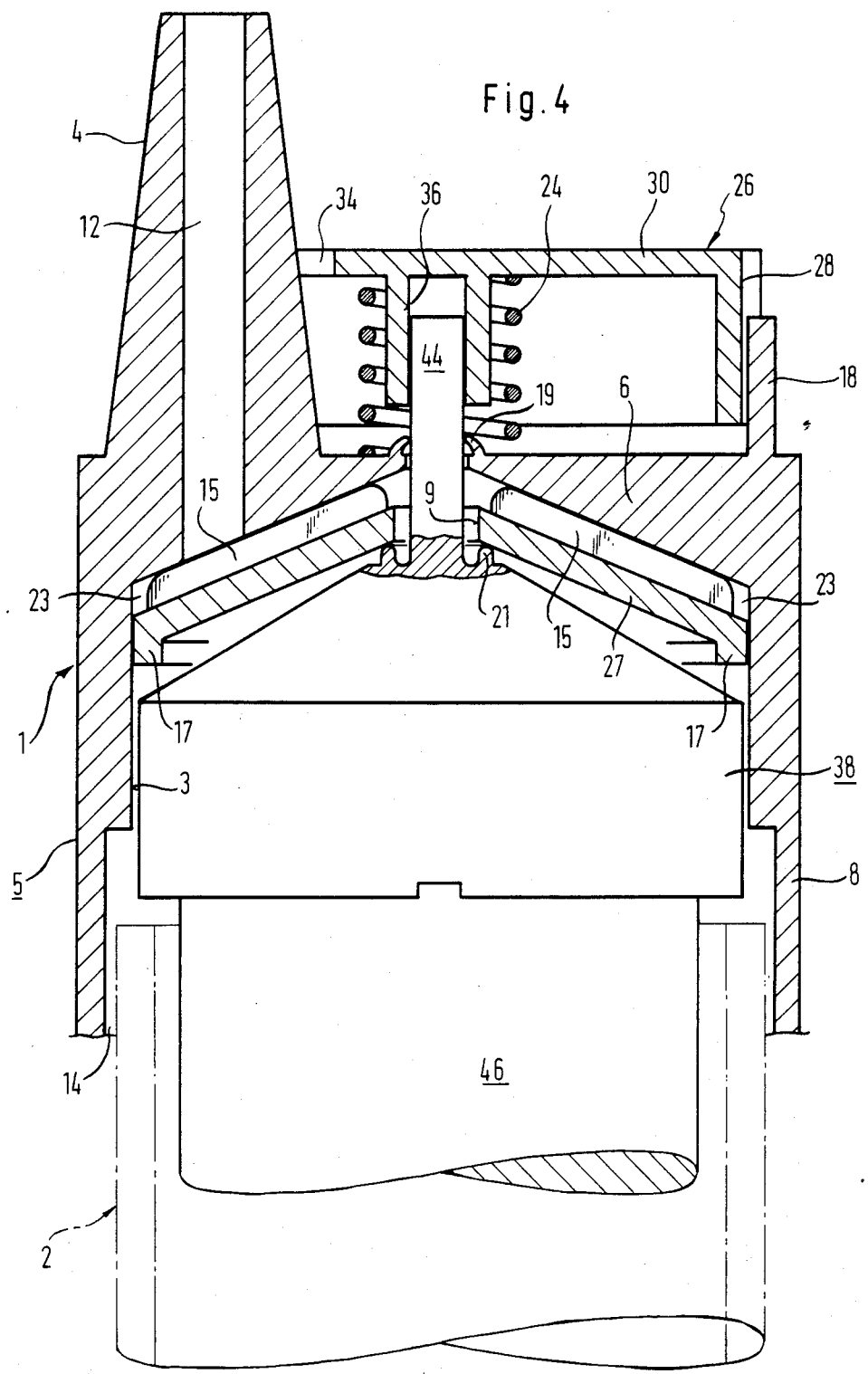
FIG. 4 a vertical section, similar to FIG. 2, but through a third embodiment.

FIG. 4 shows a third embodiment of the invention which is similar to the embodiment according to FIG. 3 to a large extent. Same parts are again provided with same reference numerals. The embodiment of FIG. 4 differs from the embodiment according to FIG. 3 in the shape of partition 27 which has the shape of a cone-like head instead of a flat plate. Partition 27 is again provided with radially extending ribs 15 on its top side which form a space between base 6 and partition 27 and thereby form a cone-like flow channel 23. The periphery 17 of partition 27 extends again downwards in axial direction to make it better conform to the inner wall of cap 1. In the center of partition 27 middle bore 9 is provided for receiving tip 44 of closing member 38, said middle bore 9 again forming the annular space mentioned in connection with FIG. 3 for passing blood. Ring collar 21 again seals flow channel 23 relative to the interior of tube 2, said ring collar in the embodiment of FIG. 4 directly contacting the lower side of partition 27. The lower side of partition 27 therefore forms a valve seat. The expert knows that an additional valve seat can be provided if necessary, e.g., if the angle of the lower side of partition 27 does not form a seat which reliably seals flow channel 23. With the exception of compression spring 24, all the components of cap 1 shown in FIGS. 1 through 4 are appropriately injection molded from plastic. According to another construction, tip 44 is connected by means of a frangible section, having a predetermined breaking point, to closing member 38, whilst separating member 46 is integrally formed with the latter. This is indicated, by way of example, in dotted lines 46 in FIG. 3. Thus, during centrifuging after reaching a predetermined g-number the frangible section breaks and releases separating member 46. During centrifuging therefore a preseparation will be effected without separating element during the initial phase of centrifuging with the separating member 46 being separated from the closing member 38 only after increasing the speed to a predetermined value.

The cap according to the invention has the advantage that it can be used in connection with normal cannulas which normally are provided with a "Luer" cone, which is a cone of a small angle of a few degrees. By eccentrically arranging the cannula cone 4 and due to pushbutton 26 the tube 2 can be handled with one hand only with the cap 1 and its tube 2 which is screwed into said cap or latched to it by some other means are held between thumb and middle finger to punctuate a blood vessel while the forefinger rests on the pushbutton 26. Whether a blood vessel has actually been punctuated can be determined by briefly pushing pushbutton 26 which was not possible in prior art devices. Further, the vacuum within the tube 2 and used for sucking blood can be shut off by closing the valve in cap 1 if a vein collapses.

As is well understood, differently structured actuation elements can be used instead of the pushbutton for one-hand handling of the cap, such actuating elements being for e.g. keys, levers or other means which can be moved back to their initial position by plastic spring means or without any spring elements by actuating one or more levers.

It will further be appreciated that the vacuum within the tube need not necessarily be generated by pulling the piston, instead it can be provided prior to use in that the tube is evacuated during manufacturing. This can be done in different ways, for e.g. by assembling within a vacuum chamber or by providing a check valve through which the tube can be evacuated or by any other means well known to the expert in this field.

What is claimed is:

1. A cap for a tube for extracting blood or the like using a needle which has a hub, comprising:
    a base having an axis, including a receiving surface means for receiving a blood tube attached thereto,
    cannula cone means, parallel to said axis of the base, for receiving the hub of the needle, extending from the base, and having a bore therethrough,
    said base having a first and a second opening therethrough which are spaced from one another, said first opening being in communication with said bore of said cannula cone means and with said second opening thereof,
    valve means for selectively closing said second opening, said valve means including a stem extending through said second opening in said base, and
    pushbutton means, movably mounted on said base, for allowing opening of said valve means by movement of said pushbutton means toward said base.

2. A cap according to claim 1, wherein the stem of said valve means engages a stem receiver disposed below said pushbutton, and wherein the stem receiver is surrounded by a spring means supported between said pushbutton and said base.

3. A cap according to claim 1, wherein said valve means has a closing surface which is a conical surface for sealing the opening.

4. A cap as in claim 1 wherein said blood tube has an axis, and an axis of said cannula cone means is located substantially parallel to said tube axis.

5. A cap for extracting blood using a blood tube which has an axis and a needle comprising:
    means for receiving a hub of the needle, said receiving means extending parallel to said axis of the blood tube and formed with a bore extending therethrough and opening at both ends thereof;
    a base, to which said receiving means is coupled, a base, to including: (a) means for coupling to the blood tube, (b) an interior bore adapted to be in registry with said blood tube when tube is coupled to said coupling means, and (c) an said blood opening in registry with one of said openings in said receiving means and with said interior bore;
    means for selectively blocking fluid communication between said opening in said receiving means and said blood tube; and means for actuating said blocking means.

6. A cap as in claim 5 wherein said receiving means has an outer surface which is tapered from one end towards the other end.

7. A cap as in claim 5 wherein said blocking means is a valve.

8. A cap as in claim 6 wherein said valve is capable of movement in directions substantially parallel to an axis of the blood tube and wherein said actuating means is a pushbutton.

9. A cap as in claim 7 wherein said valve is normally closed, and includes an opening, and the actuation thereof opens the opening to permit fluid flow therethrough.

10. A cap as in claim 5 further comprising a needle having an axis parallel to an axis of the receiving means and a blood tube coupled to said coupling means of said base.

11. A cap as in claim 5 wherein said blocking means is also for allowing a vacuum to be created in said blood tube, and wherein said actuating means is also for coupling said vacuum to said opening in said receiving means.

12. A cap as in claim 11 wherein said receiving means is a cannula cone.

13. An apparatus for receiving a needle and a blood tube which has an axis coupled thereto for extracting blood or the like, comprising:
   means for receiving a hub of the needle, said receiving means formed with an inner bore which extends from a first end to a second end and is open at both ends, and having an outer surface with a cross-section which is substantially a circle, such circle having a diameter which gradually increases from said first end toward said second end, an axis of said inner bore and of each of said circular cross-sections being parallel to said of said blood tube;
   a base, including means for coupling to the blood tube and forming a fluid-tight seal therewith, and an inner area;
   means for selectively blocking fluid flow between said opening in said inner bore in said second end of said receiving means and said inner area of said base, said blocking means having a closed position in which said inner area is isolated from said bore of said receiving means for allowing said inner area to hold a vacuum and for blocking blood flow thereinto; and
   means for selectively removing said blocking means from said closed position.

14. An apparatus as in claim 13 wherein said blocking means is a valve.

15. An apparatus as in claim 14 wherein said valve is capable of movement in a direction substantially parallel to an axis of said blood tube.

16. An apparatus as in claim 15 further comprising a blood tube, coupled to said base; and a needle coupled to said receiving means and having an axis parallel to said axis of said receiving means.

* * * * *